(12) United States Patent
Wollenweber (10) Patent No.: US 8,712,137 B2
(45) Date of Patent: Apr. 29, 2014

(54) METHODS AND SYSTEM FOR DISPLAYING SEGMENTED IMAGES

(75) Inventor: Scott David Wollenweber, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 71 days.

(21) Appl. No.: 13/482,660

(22) Filed: May 29, 2012

(65) Prior Publication Data

US 2013/0322716 A1    Dec. 5, 2013

(51) Int. Cl.
G06K 9/00    (2006.01)
G06K 9/34    (2006.01)

(52) U.S. Cl.
USPC .......................................... 382/131; 382/173

(58) Field of Classification Search
USPC .................. 382/131, 132, 128, 100, 164, 173
See application file for complete search history.

(56) References Cited

U.S. PATENT DOCUMENTS

| 7,177,953 B1 | 2/2007 | Jackson et al. | |
| 7,756,310 B2 * | 7/2010 | Manjeshwar et al. | 382/128 |
| 7,953,265 B2 | 5/2011 | Sirohey et al. | |
| 2012/0114206 A1 * | 5/2012 | Avinash et al. | 382/131 |
| 2013/0050239 A1 * | 2/2013 | Karssemeijer et al. | 345/589 |

* cited by examiner

*Primary Examiner* — Yon Couso
(74) *Attorney, Agent, or Firm* — General Electric Company; Lucas Divine (57) ABSTRACT

A method for displaying a segmented two-dimensional (2D) image includes obtaining a three-dimensional (3D) volume dataset corresponding to an imaged volume along a viewing plane, segmenting an object of interest within 3D volume to generate a plurality of segmented two-dimensional (2D) images along the viewing plane, selecting a reference image for viewing from the plurality of segmented 2D images, and displaying the reference image, the reference image having a first segmentation boundary drawn around the object of interest and a second segmentation boundary drawn around the object of interest, the first segmentation boundary being derived from the segmentation performed on the reference image and the second segmentation boundary being derived from the segmentation performed on at least one non-reference image of the plurality of segmented 2D images.

18 Claims, 8 Drawing Sheets

FIG. 9

METHODS AND SYSTEM FOR DISPLAYING SEGMENTED IMAGES

BACKGROUND OF THE INVENTION

The subject matter disclosed herein relates generally to imaging systems, and more particularly to methods and system for displaying segmented images.

Segmentation is commonly used to outline objects and/or regions within three-dimensional (3D) image volumes. For example, 3D image volumes may be segmented for surgical planning, for radiation planning, and/or for general object identification. Typically, at least some of the segmented slices are displayed as two-dimensional (2D) images. However, viewing the 2D images or slices of the segmented volume to ascertain a size or dimension of the object may be tedious and time consuming.

For example, a single 2D image may be for example, approximately 3 mm thick. For a focal tumor, looking at the segmentation in the plane defined by the location of the tumor may be sufficient to enable the user to perform surgical planning, radiation planning, and/or for general object identification. For an extended tumor or a tumor having an ill-defined shape, the tumor may extend beyond the boundaries of the tumor shown in the single 2D image. More specifically, the user may view the single 2D image and assume that the full extent of the tumor is shown. However, the tumor may appear to be smaller, larger, or have a different shape in different 2D images in parallel planes. If the full extent of the segmentation is not manually checked by the user in all planes that contain tumor as defined by the segmentation, there is a potential for error in reporting of, for example, the tumor mean value and/or the tumor volume. Further, the maximum value of the tumor may be defined by a nearby high-uptake structure and not actually within the tumor itself. Accordingly, to verify the full extent of the tumor, and perform analysis of the tumor, the user typically displays and reviews numerous 2D images. However, manually displaying and reviewing numerous 2D images is time consuming. Moreover, the difficulty and tediousness of displaying numerous 2D images, one at a time, may require a greater amount of user input than is desired.

BRIEF DESCRIPTION OF THE INVENTION

In one embodiment, a method for displaying a segmented two-dimensional (2D) image is provided. The method includes obtaining a three-dimensional (3D) volume dataset corresponding to an imaged volume along a viewing plane, segmenting an object of interest within 3D volume to generate a plurality of segmented two-dimensional (2D) images along the viewing plane, selecting a reference image from the plurality of segmented 2D images, and displaying the reference image, the reference image having a first segmentation boundary drawn around the object of interest and a second segmentation boundary drawn around the object of interest, the first segmentation boundary being derived from the segmentation performed on the reference image in the viewed plane and the second segmentation boundary being derived from the segmentation performed on at least one non-reference image not in the currently-viewed plane of the plurality of segmented 2D images.

In another embodiment, a system for displaying a segmented 2D image is provided. The system includes a medical imaging scanner, and a computer coupled to the medical imaging scanner. The computer is configured to obtain a three-dimensional (3D) volume dataset corresponding to an imaged volume along a viewing plane from the medical imaging scanner, segment an object of interest within 3D volume to generate a plurality of segmented two-dimensional (2D) images along the viewing plane, receive an input selecting a reference image from the plurality of segmented 2D images, and automatically display the reference image, the reference image having a first segmentation boundary drawn around the object of interest and a second segmentation boundary drawn around the object of interest, the first segmentation boundary being derived from the segmentation performed on the reference image and the second segmentation boundary being derived from the segmentation performed on at least one non-reference image of the plurality of segmented 2D images.

In a further embodiment, a non-transitory computer readable medium is provided. The non-transitory computer readable medium is encoded with a program programmed to instruct a computer to obtain a three-dimensional (3D) volume dataset corresponding to an imaged volume along a viewing plane from the medical imaging scanner, segment an object of interest within 3D volume to generate a plurality of segmented two-dimensional (2D) images along the viewing plane, receive an input selecting a reference image from the plurality of segmented 2D images, and automatically display the reference image, the reference image having a first segmentation boundary drawn around the object of interest and a second segmentation boundary drawn around the object of interest, the first segmentation boundary being derived from the segmentation performed on the reference image and the second segmentation boundary being derived from the segmentation performed on at least one non-reference image of the plurality of segmented 2D images.

DETAILED DESCRIPTION OF THE INVENTION

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Described in various embodiments herein is an Advanced Tumor Layout and Summary (ATLaS) module 50. In some embodiments, the ATLaS module 50 is configured to obtain a 3D volume data set corresponding to an imaged volume, the 3D volume dataset including a plurality of slices acquired along a plane, position a 3D bounding box around an object of interest in the 3D volume data set, segment the object of interest within the bounding box to generate a plurality of slices of the object of interest along the plane, and display a two-dimensional (2D) image of a first slice, the 2D image having a first segmentation boundary drawn around the object of interest in the first slice and a second segmentation boundary drawn around the object of interest in a second different slice.

Figure 1:
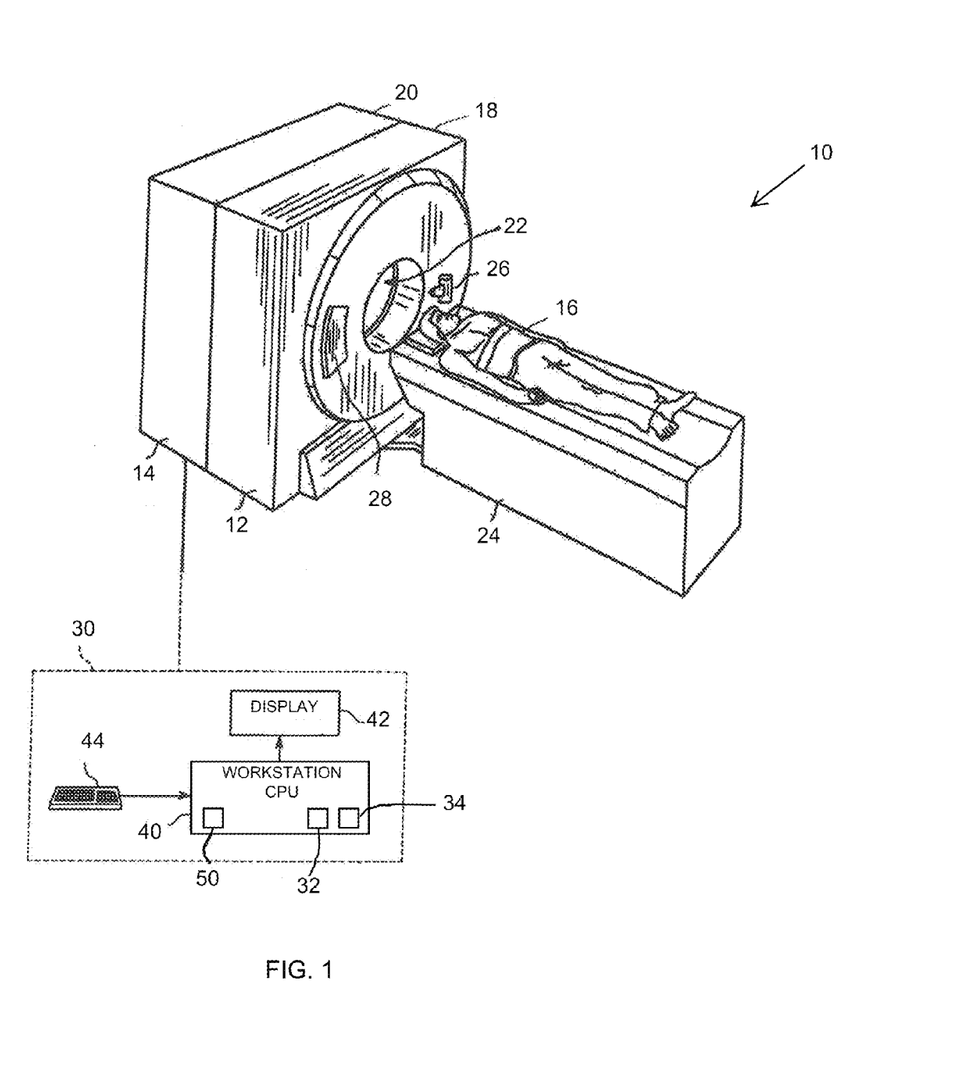
FIG. 1 is a pictorial view of an exemplary imaging system formed in accordance with various embodiments.

The ATLaS module 50 may be utilized with an imaging system such as the imaging system 10 as shown in FIG. 1. In various embodiments, the imaging system 10 is a multi-modality imaging system that includes different types of imaging modalities, such as Positron Emission Tomography (PET), Single Photon Emission Computed Tomography (SPECT), Computed Tomography (CT), ultrasound, Magnetic Resonance Imaging (MRI) or any other system capable of generating diagnostic images.

In the illustrated embodiment, the imaging system 10 is a CT/PET system. It should be realized that the various embodiments are not limited to multi-modality medical imaging systems, but may be used on a single modality medical imaging system such as a stand-alone CT imaging system or a stand-alone PET system, for example. Moreover, the various embodiments are not limited to medical imaging systems for imaging human subjects, but may include veterinary or non-medical systems for imaging non-human objects, etc.

Referring to FIG. 1, the multi-modality imaging system 10 includes a first modality unit 12 and a second modality unit 14. In the illustrated embodiment, the first modality unit 12 is a CT imaging system and the second modality unit is a PET system. The two modality units enable the multi-modality imaging system 10 to scan an object or subject 16 in a first modality using the first modality unit 12 and to scan the subject 16 in a second modality using the second modality unit 14. The multi-modality imaging system 10 allows for multiple scans in different modalities to facilitate an increased diagnostic capability over single modality systems.

The imaging system 10 is shown as including a gantry 18 that is associated with the first modality unit 12 and a gantry 20 that is associated with the second modality unit 14. During operation, the subject 16 is positioned within a central opening 22, defined through the imaging system 10, using for example, a motorized table 24. An x-ray source 26 projects a beam of x-rays through the subject 16. After being attenuated by the subject 16, the x-rays impinge on a detector 28 located on the opposite side of the gantry 18.

The imaging system 10 also includes an operator workstation 30. During operation, the motorized table 24 moves the subject 16 into the central opening 22 of the gantry 18 and/or the gantry 20 in response to one or more commands received from the operator workstation 30. The workstation 30 then operates the first and/or second modality units 12 and 14 to both scan the subject 16 and to acquire an attenuation projection data set 32 and/or an emission image dataset 34. The workstation 30 may be embodied as a personal computer (PC) that is positioned near the imaging system 10 and hard-wired to the imaging system 10 via a communication link 36. The workstation 30 may also be embodied as a portable computer such as a laptop computer or a hand-held computer that transmits information to, and receives information from the imaging system 10. Optionally, the communication link 36 may be a wireless communication link that enables information to be transmitted to and/or from the workstation 30 to the imaging system 10 wirelessly. In operation, the workstation 30 is configured to control the operation of the imaging system 10 in real-time. The workstation 30 is also programmed to perform medical image diagnostic acquisition and reconstruction processes described herein.

The operator workstation 30 includes a central processing unit (CPU) or computer 40, a display 42, and an input device 44 (e.g., a mouse, and/or a keyboard). As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 40 executes a set of instructions that are stored in one or more storage elements or memories, in order to process information received from the first and second modality units 12 and 14. The storage elements may also store data or other information as desired or needed. The storage element may be in the form of an information source or a physical memory element located within the computer 40.

The imaging system 10 also includes the ATLaS module 50 that is configured to implement various methods described herein. The ATLaS module 50 may be implemented as a piece of hardware that is installed in the computer 40. Optionally, the ATLaS module 50 may be implemented as a set of instructions that are installed on the computer 40. The set of instructions may be stand alone programs, may be incorporated as subroutines in an operating system installed on the computer 40, may be functions in an installed software package on the computer 40, and the like. It should be understood that the various embodiments are not limited to the arrangements and instrumentality shown in the drawings.

Figure 2:
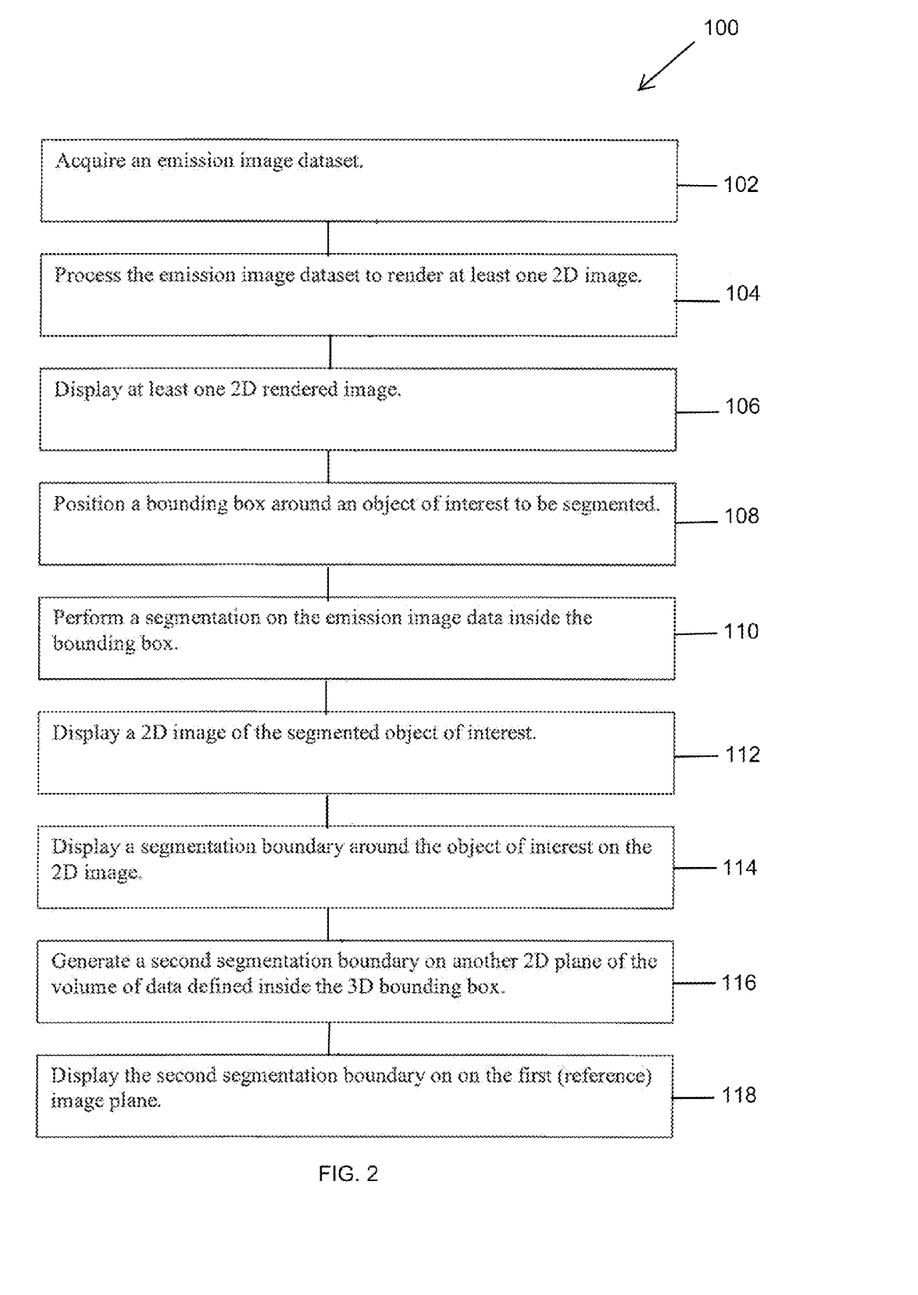
FIG. 2 is a flowchart illustrating a method for displaying an image in accordance with various embodiments.
Figure 3:
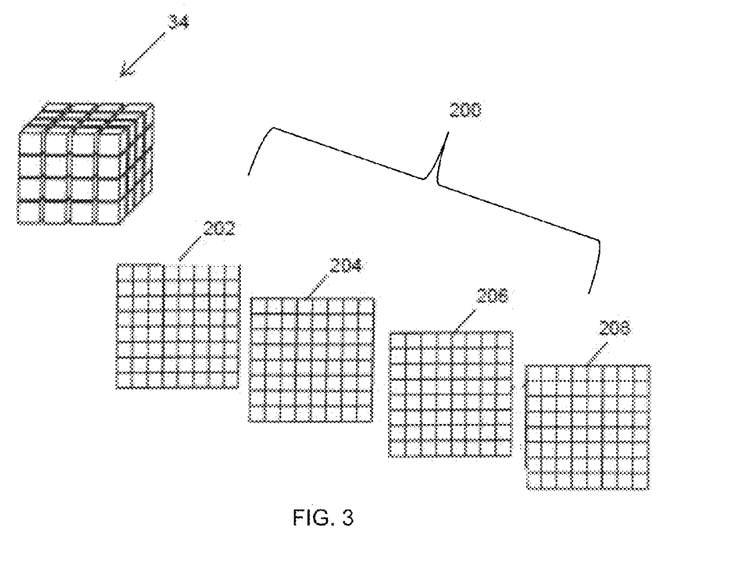
FIG. 3 is block diagram of an exemplary dataset that may be acquired in accordance with various embodiments.

FIG. 2 is a flowchart of an exemplary method 100 for displaying a 2D image of an object of interest. In various embodiments, the method 100 may be implemented using for example, the ATLaS module 50. At 102, an emission image dataset, such as the emission image dataset 34 is acquired. The emission image dataset 34 is a three-dimensional (3D) volume of information (as shown in FIG. 3) having a plurality of image voxels corresponding to image data. It should be noted that the 3D emission image dataset 34 is generally formed from a plurality of 2D image slices arranged in a stack. For example, as shown in FIG. 3, the emission image dataset 34 may be formed from a plurality of slices 200, including a first slice 202, a second slice 204, a third slice 206, and an nth slice 208. It should be realized that the emission image dataset 34 may be utilized to form a plurality of slices in three orthogonal axes. For example, the emission image dataset 34 may include a plurality of slices along a first axis to form a sagittal view of the subject 16, a plurality of slices along a second axis to form an axial view of the subject 16, and a plurality of slices along a third axis to form a coronal view of the subject 16.

In operation, to generate the emission image dataset 34, the imaging system 10 performs a scan of, for example, the subject 16. In various embodiments, the imaging system 10 is configured to perform a scan of a region of interest that includes, for example, a tumor or lesion. Emission image dataset 34, as used herein, is a set of 3D data that is represented by three orthogonal axes acquired over a predetermined time period of, for example, the tumor and at least some of the regions surrounding the tumor. It should be realized that although various embodiments are described with respect to imaging a tumor, the various embodiments may also be utilized to image other objects or organs and the tumor is an example of one such object.

Figure 4:
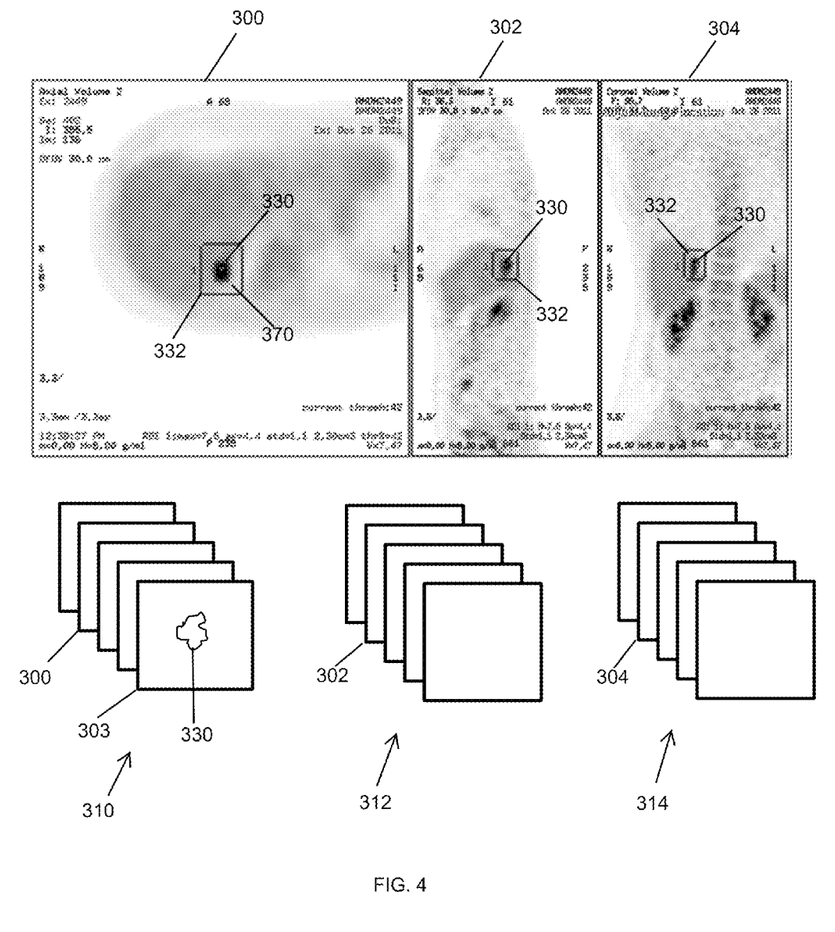
FIG. 4 is a plurality of images that may be displayed in accordance with various embodiments.

At 104, the emission image dataset 34 is processed, or rendered, to generate at least one 2D image or slice of the subject 16. In various embodiments, the emission image dataset 34 is processed, or rendered, to generate a plurality of 2D images or slices of the subject 16. For example, FIG. 4 is a pictorial view of an exemplary 2D axial image 300, a 2D sagittal image 302, and a 2D coronal image 304 that may be rendered at 104. It should be realized that because the emission image dataset 34 is acquired along three orthogonal axes, that the emission image dataset 34 includes an axial volume of emission information that may be utilized to construct a plurality of axial 2D images 310, wherein the 2D axial image 300 represents one such image. Moreover, the emission image dataset 34 includes a sagittal volume of emission information that may be utilized to construct a plurality of sagittal 2D images 312 wherein the 2D sagittal image 302 represents one such image, and the emission image dataset 34 includes a coronal volume of emission information that may be utilized to construct a plurality of coronal 2D images 314, wherein the 2D coronal image 304 represents one such image. Accordingly, the emission image dataset 34 may be utilized to render a plurality of slices in three orthogonal axes which may then be utilized to generate a plurality of 2D images.

In various embodiments, at least a portion of the emission image dataset 34 may rendered based on 3D rendering settings. By rendering "at least a portion" of the emission image dataset 34, it is meant that the entire emission image dataset 34 or a subset of the emission image dataset 34 may be rendered, for example, such that an image is reconstructed or formed from the data. The 3D rendering settings used to render the emission image dataset 34 determine how one or more images of the emission image dataset 34 will be viewed by a user. The 3D rendering settings may include, but are not limited to, orientation, the type of renderer (e.g., volume rendering, maximum intensity projection (MIP), etc.), a depth setting, a clipping setting, a thickness setting, an opacity map, and/or the like. Referring again to FIG. 2, at 106, at least one of the rendered 2D images, 300, 302, and/or 304 is then displayed based on the 3D rendering settings.

At 108, a bounding box 332 is positioned around an object of interest that is to be segmented. More specifically, in some embodiments, a 2D segmentation may be manually performed by the user by drawing or virtually tracing on a screen a bounding box 332 (shown in FIG. 4) that encloses an object or region 330 the user desires to be segmented from the emission image dataset 34. For example, as shown in FIG. 4, the user may draw the bounding box 332 around the tumor 330 using an input device, such as, but not limited to, a mouse, a touch pad, a pointer, a stylist, and/or the like. In other embodiments, the 2D segmentation may be performed semi-automatically or fully-automatically using a computer (e.g., the computer 40 shown in FIG. 1). For example, when the 2D segmentation is semi-automatically created, the user may position a seed point (not shown) on the tumor 330, the computer 40 may then create the 2D segmentation (e.g., using a live-wire-based segmentation, seeded watershed segmentation, and/or the like). One example of fully automatic 2D segmentation using a computer includes, but is not limited to, automatic thresholding. In various embodiments, the user may modify the bounding box 332 with the input device 44, such as to change a size or position relative to the tumor 330 as is described in more detail below.

Referring again to FIG. 2, at 110, a 2D segmentation of at least one of the rendered 2D images 300, 302, and/or 304 is performed based on the bounding box 332 described above. In various embodiments, and referring again to FIG. 4, the object of interest selected to be segmented is the tumor 330. The 2D segmentation of a rendered 3D volume data, such as the 2D axial image 300, may be created using any suitable method, process, means, structure, and/or the like.

In operation, the segmentation may be performed using a segmentation algorithm. The segmentation algorithm uses a principle, whereby it is generally assumed that various organs, tissue, fluid, and other anatomical features, surrounding the tumor 330 may be differentiated from the tumor 330 by determining the intensity of each voxel in the image data. The intensity generally represents the value of the voxel. Based on the intensity values of each of the voxels, the tumor 330 may be distinguished from the other anatomical features. Accordingly, at 110 the segmentation algorithm is configured to automatically compare the intensity value for each voxel in the emission image dataset 34 to a predetermined intensity value, using for example, a thresholding process. In the exemplary embodiment, the predetermined intensity value may be a range of predetermined intensity values. The predetermined value range may be automatically set based on a priori information of the tumor 330. Optionally, the predetermined range may be manually input by the operator. In one embodiment, if the intensity value of a voxel is within the predetermined range, the voxel is classified as belonging to the tumor 330. Otherwise, the voxel is classified as not belonging to the tumor 330. It should be realized that the segmentation algorithm may also be utilized with other segmentation techniques to identify the tumor 330. Additionally, as should be appreciated, other suitable segmentation algorithms may be used.

Figure 5:
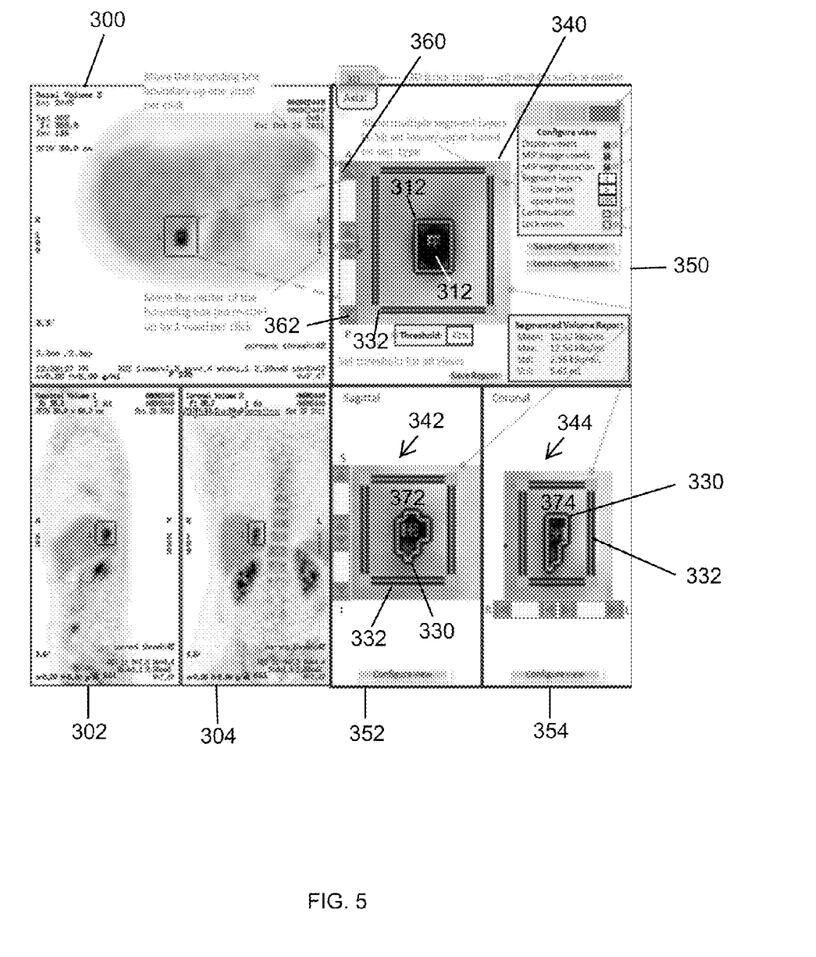
FIG. 5 is a plurality of viewports that may be generated in accordance with various embodiments.

At 112, the segmented information of the tumor 330 identified at 110 is utilized to generate and display at least one 2D image of the segmented tumor 330. For example, FIG. 5 illustrates a plurality of exemplary 2D surface renderings of the tumor 330 that may be generated and displayed using the information acquired at 110. In various embodiments, the ATLaS module 50 is configured to display a plurality of segmented 2D images concurrently with the associated 2D image utilized to perform the segmentation. For example, in various embodiments, the 2D axial image 300 may be displayed concurrently with a 2D segmented axial image 340, the 2D sagittal image 302 may be displayed concurrently with a 2D segmented sagittal image 342, and the 2D coronal image 304 may be displayed concurrently with a 2D segmented coronal image 344. It should be realized that the segmented images 340, 342, 344 may also be shown separately from the 2D images 300, 302, 304. Moreover, it should be realized that a single segmented image may be shown with a single non-segmented image.

In various embodiments, the segmented images 340, 342, and 344 are displayed in different viewports. A viewport, as used herein, is a framed area on a display, such as the display 42, for viewing information. Accordingly, in various embodiments, the segmented axial image 340 is displayed in a viewport 350, the segmented sagittal image 342 is displayed in a viewport 352, and the segmented coronal image 344 is displayed in a viewport 354. In operation, the viewports 350, 352, and 354 enable the operator to manipulate various portions of the segmented images. For example, as shown in FIG. 5, the viewports 350, 352, and 354 each display a magnified and/or rotatable image of the segmented tumor 330. In various embodiments, the viewports 350, 352, and 354 enable the user to modify a location of the bounding box 332. For example, the viewport 350 includes an icon 360 that enables the user to move the bounding box 332 up one voxel per click and an icon 362 that enables the user to move the bounding box 332 down one voxel per click. Alternatively, the icons 360 and 362 can be configured to change the size of the bounding box up and down by clicking. The viewports 352 and 354 also include the same icons to enable the user to modify the location of the bounding boxes 332 shown in the viewports, respectively. Accordingly, in one embodiment, the user may utilize the icons 360 and 362 to modify the size of the bounding box 332. In other embodiments, the user may select the bounding box 332, using for example a mouse, and manually modify the size, shape or location of the bounding box 332 using the mouse.

As shown in FIG. 5, the viewports 350, 352, and 354 also include visual indicators, referred to herein as segmentation boundaries, that depict or encapsulate the object being segmented, e.g. the tumor 330. It should be realized that the area within the segmentation boundary includes voxels that were previously identified in the segmentation process as belonging to the tumor 330. Moreover, the area outside the segmentation boundary represents the voxels that were previously identified in the segmentation process as not belonging to the tumor 330. Thus, the segmentation boundaries represent a line that encapsulates the tumor 330.

Accordingly, and referring again to FIG. 2, at 114 a segmentation boundary is drawn around the object of interest. For example, as shown in FIG. 5, the viewport 350 includes a segmentation boundary 370 that encloses the tumor 330, the viewport 352 includes a segmentation boundary 372 that encloses the tumor 330, and the viewport 354 includes a segmentation boundary 374 that encloses the tumor 330. It should be realized that the segmentation boundaries may be have different shapes depending on the shape of the tumor 330 in each image plane being segmented. For example, as described above, the tumor 330 shown in the 2D axial image 340 has a segmentation boundary 370 having a first shape. Whereas the tumor 330 shown in the 2D sagittal image 342 and the 2D coronal image 344 have segmentation boundaries 372 and 374, respectively that have shapes that are different than the segmentation boundary 370.

Figure 6:
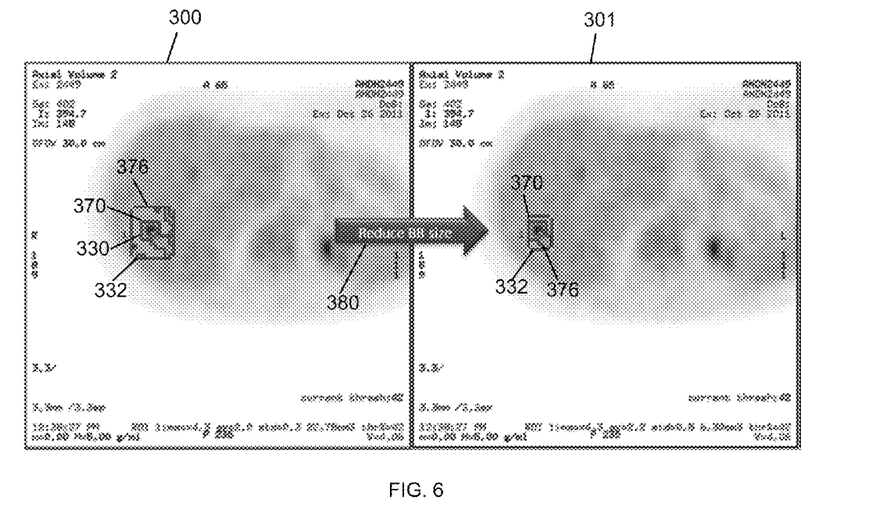
FIG. 6 is another plurality of images that may be displayed in accordance with various embodiments.

It should be realized that in the exemplary embodiment, the segmentation boundary 370, for example, encapsulates substantially only the tumor 330. However, in some embodiments, the segmentation boundary 370 may also include voxels that are not part of the tumor 330 due to surrounding structures of similar image intensity as the tumor. Accordingly, and as shown in FIG. 6, in various embodiments the user may modify the size of the bounding box 332, using for example, the icons 360 and 362 and repeat the segmentation process to generate a revised set of segmented images displayed in the respective viewer. For example, the user may resize the bounding box, as is described in more detail below, in the segmented 2D axial image 300 to generate a revised segmented axial image 301. In various embodiments, the image 300 may be displayed concurrently with the revised image 301. Moreover, a visual indicator 380 may be displayed to indicate that the bounding box 332 has been modified as described above.

Referring again to FIG. 2, at 116 a second segmentation boundary on another 2D plane of the volume of data defined inside the 3D bounding box is generated. More specifically, in various embodiments, the shape of the tumor 330 and inclusion of non-tumor voxels within the segmentation inside the bounding box may vary from slice to slice. For example, as described above, the emission image dataset 34 is acquired along three orthogonal axes to acquire an axial volume of emission information, a sagittal volume of emission information, and a coronal volume of information. Moreover, each of the axial, sagittal, and coronal volumes includes a plurality of slices. For example, the axial volume includes a plurality of axial 2D images 310 (shown in FIG. 4) of which the 2D axial image 300 (shown in FIG. 5) represents one such image slice. Accordingly, in various embodiments, a segmentation boundary is calculated for the tumor 330 in each of the slices for each volume. More specifically, a segmentation boundary may be derived for each of the axial 2D images 310, the sagittal 2D image 312, and the coronal 2D images 314.

However, in some instances, the tumor 330 may have a non-uniform shape. For example, referring again to FIG. 4, the tumor 330 may have a substantially round shape in the 2D axial image 300 and a different shape in an 2D axial image 303. More specifically, the shape of the tumor 330 may vary from slice to slice along the same viewing plane in the same set of slices. However, as discussed above, it is often tedious and time consuming for a user to manually review each image slice to determine the changes in the shape of the tumor.

Accordingly, at 118 the segmented 2D reference image is revised to include a second segmentation boundary. For example, and referring to FIG. 7, the 2D axial image 402 with segmentation boundary 384 may be revised as shown in image 404 to include a second segmentation boundary 386 that is displayed concurrently with the first segmentation boundary 384. In various embodiments, the second segmentation boundary 386 represents the segmentation boundary derived from at least one of the slices forming the plurality of slices taken along a single view. For example, in one embodiment, the second segmentation boundary 386 may represent the segmentation boundary derived for the 2D axial image 303 (shown in FIG. 4). The segmentation boundary derived for the 2D axial image 303 is then superimposed onto the 2D axial image 300 such that the 2D axial image 300 displays the segmentation boundary 370 as derived from information acquired from the 2D axial image 303. In various other embodiments, the second segmentation boundary 376 may represent the segmentation boundary derived for a plurality of slices.

For example, and referring again to FIG. 4 assume that the 2D axial image 300 is selected as a reference slice. The user then draws the bounding box 332 on the 2D axial image 300 to perform a segmentation of the tumor 330. The 2D axial image is then displayed including the segmentation boundary 370 of the tumor 330 as derived from the 2D axial image 300. Moreover, the 2D axial image 300 also displays the second segmentation boundary 376 that represents the combined segmentation boundaries derived from the remaining images in the set of 2D axial images 310. In various embodiments, displaying a respective 2D image that includes the segmentation boundary for the image and the segmentation boundaries for additional images enables a user to ascertain changes in the shape of the tumor 330 without having to view additional slices. More, specifically, a user can view a single image and determine whether the shape of the tumor is changing from image to image along the same plane or if there are segmentation boundaries from other image planes parallel to the reference image not connected to the current in-image tumor border 370.

In various embodiments, the first segmentation boundary 370 may be displayed using a first color and the second segmentation boundary 376 may be displayed using a second different color. In other embodiments, the first segmentation boundary 370 may be displayed using a line having a first style, e.g. a solid line, and the second segmentation boundary 376 may be displayed using a line having a second style, e.g. a dashed line.

Figure 7:
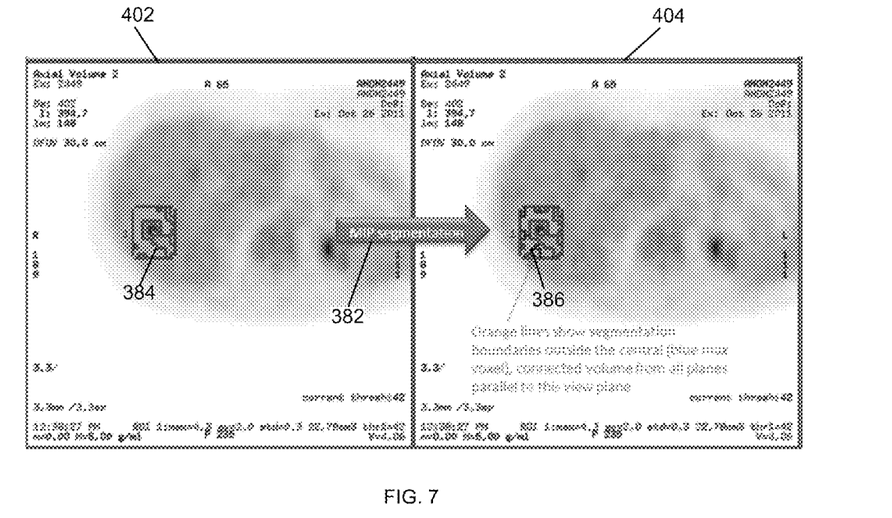
FIG. 7 is still another plurality of images that may be displayed in accordance with various embodiments.

FIG. 7 is a plurality of images 400 that may be displayed in accordance with various embodiments. In particular, maximum intensity pixel projection of the segmented tumor borders is performed through each border in the set of 2D images to generate the segmentation border shown in image 404. For example, the plurality of axial 2D images 310 may be utilized to form the MIP segmentation border 386. Moreover, the images 402 and 404 enable the user to perform various diagnostic tasks.

For example, in various embodiments, the ATLaS module 50 may be activated by the user. In operation, the ATLaS module 50 is configured to generate and display the various viewports and images described herein. Moreover, the ATLaS module 50 may also be configured to activate various icons and controls to enable the user to perform various diagnostic tasks and/or to manipulate the bounding box 332, etc. as described above. For example, the ATLaS module 50 may activate and display a visual indicator 382 that enables the user to perform the segmentation. Such diagnostic tasks include, for example, enabling the user to select various viewport configuration parameters and/or localize the bounding box 332. Moreover, the ATLaS module 50 may enable a user to select a default configuration wherein the voxels may be displayed or not displayed, the segmentation may be shown or not shown, different slices, such as an upper and lower slice may be shown, a continuation process may be activated to allow the segmentation to propagate outside the bounding box 332, etc.

Figure 8:
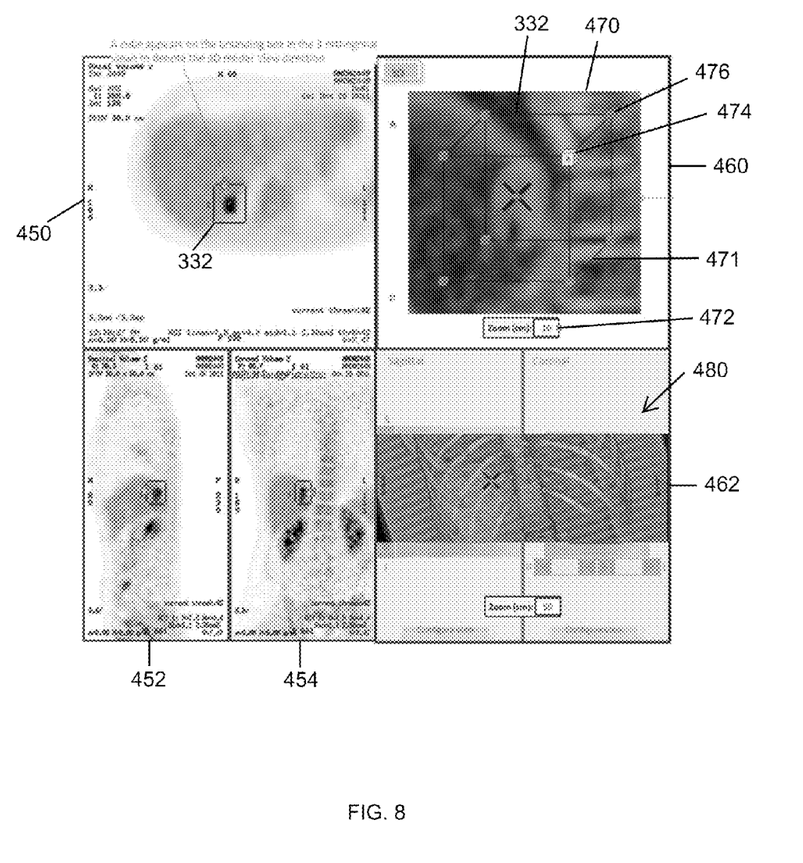
FIG. 8 are a plurality of viewports that may be generated in accordance with various embodiments.

The ATLaS module 50 may also be configured to enable the user to display a 3D image of the tumor 330. For example, FIG. 8 shows an exemplary 2D axial image 450, a 2D sagittal image 452, and a 2D coronal image 454. In various embodiments, the ATLaS module 50 may also automatically generate a viewport 460 and a viewport 462. In various embodiments, the viewports 460 and 462 are utilized to display a portion of the at least one of the images 450, 452, or 454. For example, in the illustrated embodiment, the viewport 460 is configured to display a segmented image 470 of the axial image 450 that is segmented as described above. Additionally, the ATLaS module 50 may enable the viewport 460 to enlarge or shrink the size of the image 470. For example, the viewport 460 may include a type-in box 472 that the user may modify to resize the image 470. Additionally, the viewport 460 may generate a 3D control box, that is some embodiments, may be a visual representation of the bounding box 332 in three dimensions to enable the user to determine an orientation, e.g. axial, sagittal, or coronal, of the segmented image 470. In various embodiments, the control box 471 enables the user to rotate or reorient the displayed image 470. For example, the control box 471 may include a visual indicator 474 that identifies a reference corner of the image 470. Thus, in operation, the visual indicator 474 is positioned in the same position on the image 470 regardless of the orientation of the image 470.

Moreover, the control box 471 may include a plurality of control points 476 that enable the user to manipulate the size and/or orientation of the control box 471. In the illustrated embodiment, the control points 476 are located at the corners of the control box 471. However, it should be realized that the control points 476 may be located anywhere on the control box 471. Accordingly, when the control box 471 is operated in a 3D mode, the user may manipulate the image 470 along all three axes by merely repositioning the control box 471. In various embodiments, the viewport 462 may be utilized to display an image 480 acquired from a second modality such as the CT imaging system 12. In operation, the image 480 may be displayed concurrently with the image 470 to aid in localization of the tumor 330, for example.

A technical effect is to display a single 2D image that includes a segmentation boundary drawn around an object of interest in the 2D image and a second different segmentation boundary that is derived from segmentations of the object of interest in other images generated along the same viewing plane. Accordingly, in operation, the methods and systems described herein provide the user with an improved ability to perform diagnosis while reducing the quantity of images viewed by the user to form the diagnosis.

Figure 9:
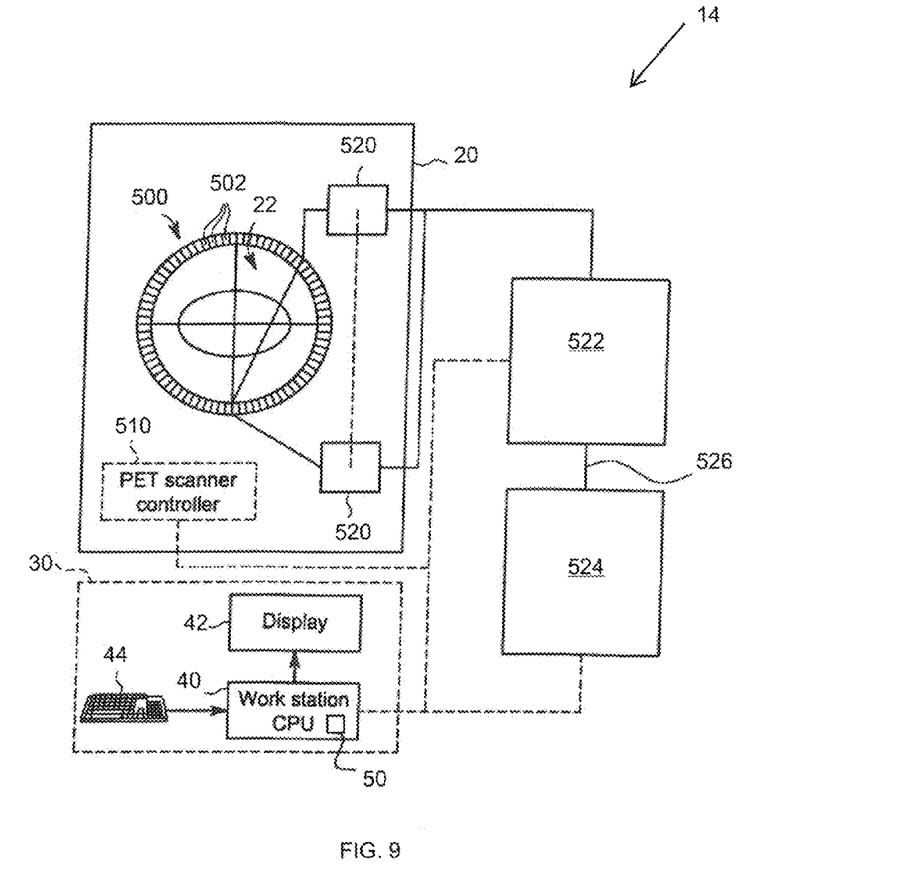
FIG. 9 is a block schematic diagram of the second modality unit shown in FIG. 1 in accordance with various embodiments.

Various embodiments of the methods and module 50, described herein may be provided as part of, or used with, a medical imaging system, such as a dual-modality imaging system 10 as shown in FIG. 1. FIG. 9 is a block schematic diagram of the second modality unit 14, e.g. the PET imaging system, shown in FIG. 1. As shown in FIG. 9, the PET system 14 includes a detector array 500 that is arranged as ring assembly of individual detector modules 502. The detector array 10 also includes the central opening 22, in which an object or patient, such as the subject 16 may be positioned, using, for example, the motorized table 24 (shown in FIG. 1). The motorized table 24 is aligned with the central axis of the detector array 500. During operation, the motorized table 24 moves the subject 16 into the central opening 22 of the detector array 500 in response to one or more commands received from the operator workstation 30. More specifically, a PET scanner controller 510 responds to the commands received from the operator workstation 30 through the communication link 32. Therefore, the scanning operation is controlled from the operator workstation 30 through PET scanner controller 510.

During operation, when a photon collides with a scintillator on the detector array 500, the photon collision produces a scintilla on the scintillator. The scintillator produces an analog signal that is transmitted to an electronics section (not shown) that may form part of the detector array 500. The electronics section outputs an analog signal when a scintillation event occurs. A set of acquisition circuits 520 is provided to receive these analog signals. The acquisition circuits 520 process the analog signals to identify each valid event and provide a set of digital numbers or values indicative of the identified event. For example, this information indicates when the event took place and the position of the scintillation scintillator that detected the event.

The digital signals are transmitted through a communication link, for example, a cable, to a data acquisition controller 522. The data acquisition processor 522 is adapted to perform the scatter correction and/or various other operations based on the received signals. The PET system 12 may also include an image reconstruction processor 524 that is interconnected via a communication link 526 to the data acquisition controller 522. During operation, the image reconstruction processor 524 performs various image enhancing techniques on the digital signals and generates an image of the subject 16.

As used herein, a set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for displaying a segmented two-dimensional (2D) image, the method comprising:
   obtaining a three-dimensional (3D) volume dataset from a computer memory, wherein the dataset corresponds to an imaged volume along a viewing plane;
   segmenting, using a computer processor, an object of interest within 3D volume to generate a plurality of segmented two-dimensional (2D) images along the viewing plane;
   selecting a reference image for viewing from the plurality of segmented 2D images;
   displaying the reference image, the reference image having a first segmentation boundary drawn around the object of interest and a second segmentation boundary drawn around the object of interest, the first segmentation boundary being derived from the segmentation performed on the reference image and the second segmentation boundary being derived from the segmentation performed on at least one non-reference image of the plurality of segmented 2D images, and
   wherein the second segmentation boundary comprises a composite segmentation boundary derived from a plurality of non-reference images generated along the viewing plane.

2. The method of claim 1, wherein the first segmentation boundary has a first color and the second segmentation boundary has a second different color.

3. The method of claim 1, wherein the first segmentation boundary has a first style and the second segmentation boundary has a second different style.

4. The method of claim 1, further comprising positioning a bounding box around the object of interest to perform the segmentation.

5. The method of claim 4, further comprising:
   modifying a size of the bounding box; and
   generating a revised segmented image based on the modified bounding box.

6. The method of claim 1, further comprising:
   defining a seed point in the object of interest;
   generating a bounding box around the object of interest based on the seed point; and
   generating a revised segmented image based on the bounding box.

7. The method of claim 1, wherein the 3D volume dataset comprises a 3D emission image dataset.

8. A system for displaying a segmented two-dimensional (2D) image, the system comprising:
   a medical imaging scanner; and
   a computer coupled to the medical imaging scanner, the computer configured to
      obtain a three-dimensional (3D) volume dataset corresponding to an imaged volume along a viewing plane from the medical imaging scanner;
      segment an object of interest within 3D volume to generate a plurality of segmented two-dimensional (2D) images along the viewing plane;

receive an input selecting a reference image for viewing from the plurality of segmented 2D images;

automatically display the reference image, the reference image having a first segmentation boundary drawn around the object of interest and a second segmentation boundary drawn around the object of interest, the first segmentation boundary being derived from the segmentation performed on the reference image and the second segmentation boundary being derived from the segmentation performed on at least one non-reference image of the plurality of segmented 2D images; and wherein the second segmentation boundary is on a separate 2D plane from the first segmentation boundary.

9. The system of claim 8, wherein the second segmentation boundary comprises a composite segmentation boundary derived from a plurality of non-reference images generated along the separate 2D plane from the first segmentation boundary.

10. The system of claim 8, wherein the first segmentation boundary has a first color and the second segmentation boundary has a second different color.

11. The system of claim 8, wherein the first segmentation boundary has a first style and the second segmentation boundary has a second different style.

12. The system of claim 8, wherein the computer is further configured to receive an input to position a bounding box around the object of interest to perform the segmentation.

13. The system of claim 8, wherein the computer is further configured to:

receive an input to modify a size of the bounding box; and automatically generate a revised segmented image based on the modified bounding box.

14. The system of claim 8, wherein the medical imaging scanner comprises a positron emission tomography (PET) system.

15. A non-transitory computer readable medium encoded with a program programmed to instruct a computer to:

obtain a three-dimensional (3D) volume dataset corresponding to an imaged volume along a viewing plane from the medical imaging scanner;

segment an object of interest within 3D volume to generate a plurality of segmented two-dimensional (2D) images along the viewing plane;

receive an input selecting a reference image for viewing from the plurality of segmented 2D images;

automatically display the reference image, the reference image having a first segmentation boundary drawn around the object of interest and a second segmentation boundary drawn around the object of interest, the first segmentation boundary being derived from the segmentation performed on the reference image and the second segmentation boundary being derived from the segmentation performed on at least one non-reference image of the plurality of segmented 2D images, receive an input to modify a size of the bounding box; and automatically generate a revised segmented image based on the modified bounding box.

16. The non-transitory computer readable medium of claim 15, wherein the second segmentation boundary comprises a composite segmentation boundary derived from a plurality of non-reference images generated along the viewing plane.

17. The non-transitory computer readable medium of claim 15, wherein the first segmentation boundary has a first color and the second segmentation boundary has a second different color.

18. The non-transitory computer readable medium of claim 15, wherein the first segmentation boundary has a first style and the second segmentation boundary has a second different style.

* * * * *